(12) United States Patent
Swift

(10) Patent No.: US 6,919,421 B2
(45) Date of Patent: Jul. 19, 2005

(54) METHODS OF SYNTHESIS OF POLYSUCCINIMIDE, COPOLYMERS OF POLYSUCCINIMIDE AND DERIVATIVES THEREOF

(75) Inventor: Graham Swift, Chapel Hill, NC (US)

(73) Assignee: Folia, Inc, Birmingham, AL (US)

( * ) Notice: Subject to any disclaimer, the term of this patent is extended or adjusted under 35 U.S.C. 154(b) by 0 days.

(21) Appl. No.: 10/698,397

(22) Filed: Nov. 3, 2003

(65) Prior Publication Data

US 2004/0092704 A1 May 13, 2004

Related U.S. Application Data

(63) Continuation-in-part of application No. 10/307,349, filed on Dec. 2, 2002, now Pat. No. 6,686,440, and a continuation-in-part of application No. 10/307,387, filed on Dec. 2, 2002, now Pat. No. 6,686,441, which is a continuation of application No. 09/776,897, filed on Feb. 6, 2001, now Pat. No. 6,495,658.

(51) Int. Cl.$^7$ ................................................ C08G 69/10
(52) U.S. Cl. ....................... 528/328; 528/310; 528/354; 528/363
(58) Field of Search ................................. 528/310, 328, 528/354, 363

(56) References Cited

U.S. PATENT DOCUMENTS

| | | |
|---|---|---|
| 6,414,050 B1 | 7/2002 | Howdle et al. |
| 6,444,772 B1 | 9/2002 | McGinniss et al. |
| 6,486,078 B1 | 11/2002 | Rangarajan et al. |
| 6,486,355 B1 | 11/2002 | Ferrieri |
| 6,589,355 B1 | 7/2003 | Thomas et al. |

Primary Examiner—Terressa Boykin
(74) Attorney, Agent, or Firm—Stamatios Mylonakis

(57) ABSTRACT

Disclosed are methods of synthesis of polysuccinimide, copolymers, derivatives and blends with additives thereof, using a supercritical fluid. Also disclosed are methods of isolating, compounding, stabilizing and processing the polysucciminide, its copolymers and derivatives.

99 Claims, 5 Drawing Sheets

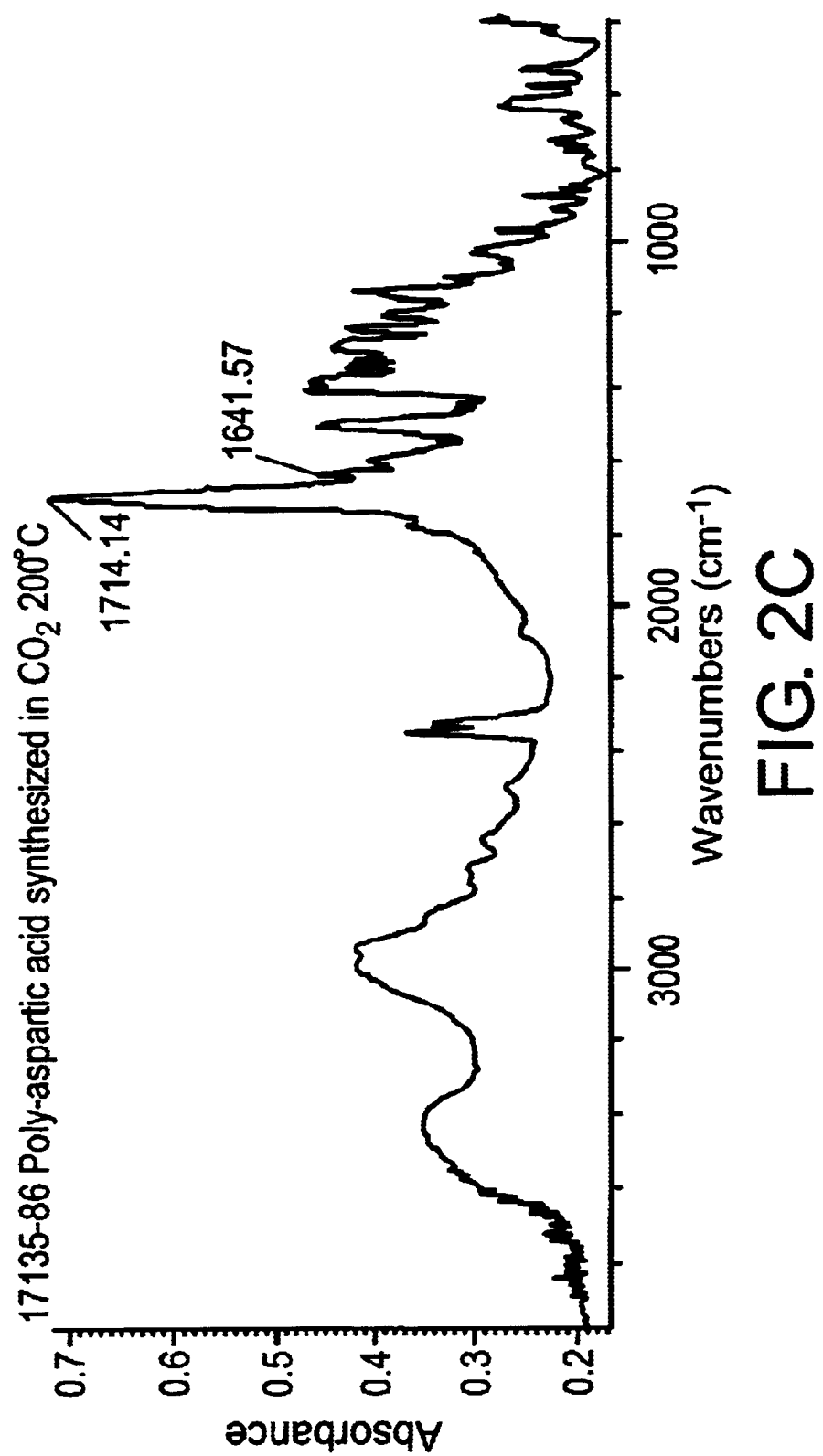

METHODS OF SYNTHESIS OF POLYSUCCINIMIDE, COPOLYMERS OF POLYSUCCINIMIDE AND DERIVATIVES THEREOF

This application is a Continuation-In-Part of application Ser. No. 10/307,349 filed Dec. 2, 2002 now U.S. Pat. No. 6,686,440 issued Feb. 3, 2004 and 10/307,387 filed Dec. 2, 2002 now U.S. Pat. No. 6,686,441 issued Feb. 3, 2004 which are a Continuation and Continuation-In-Part, respectively, of application Ser. No. 09/776,897, filed Feb. 6, 2001, now U.S. Pat. No. 6,495,658, issued Dec. 17, 2002, all three of which are incorporated herein by reference in their entirety.

BACKGROUND OF THE INVENTION

1. Field of the Invention

The present invention relates to a process for the preparation of polysuccinimide, polysuccinimide copolymers and derivatives thereof dissolved or dispersed in a supercritical fluid (SCF), such as liquid $CO_2$ or supercritical $CO_2$ in an organic cosolvent, starting with an aminoacid such as L-aspartic acid. Dewatering stage or concentration of monomers may be done by any suitable technique including wiping film evaporator, drum drying, evaporation in a screw reactor or inline concentrator, etc.

2. Discussion of the Related Art

L-aspartic acid has been produced commercially since the 1980's via immobilized enzyme methods. The L-aspartic acid so produced mainly has been used as a component of the synthetic sweetener, N-aspartylphenylalanine methyl ester (ASPARTAME®).

In a typical production pathway, a solution of ammonium maleate is converted to fumarate via action of an immobilized enzyme, maleate isomerase, by continuous flow over an immobilized enzyme bed. Next, the solution of ammonium fumarate is treated with ammonia also by continuous flow of the solution over a bed of the immobilized enzyme, aspartase. A relatively concentrated solution of ammonium asparate is produced, which then is treated with an acid, for example nitric acid, to precipitate aspartic acid. After drying, the resultant product of the process is powdered or crystalline L-aspartic acid. Prior art that exemplifies this production pathway includes U.S. Pat. No. 4,560,653 to Sherwin and Blouin (1985), U.S. Pat. No. 5,541,090 to Sakano et al. (1996), and U.S. Pat. No. 5,741,681 to Kato et al. (1998).

In addition, nonenzymatic, chemical routes to D,L aspartic acid via treatment of maleic acid, fumaric acid, or their mixtures with ammonia at elevated temperature have been known for over 150 years (see Harada, K., *Polycondensation of thermal precursors of aspartic acid. Journal of Organic Chemistry* 24, 1662–1666 (1959); also, U.S. Pat. No. 5,872,285 to Mazo et al. (1999)). The above chemical routes of maleic acid and ammonia are less sterically controlled as well as less quantitative and the product is a D,L racemic mixture. Although the non-enzymatic routines are significantly less quantitative than the enzymatic syntheses of aspartic acid, possibilities of continuous processes and recycling of reactants and by-products via chemical routes are envisioned.

Polymerization and copolymerization of L-aspartic acid alone or with other comonomers is known. As reviewed in U.S. Pat. No. 5,981,691 to Sikes (1999), synthetic work with polyamino acids, beginning with the homopolymer of aspartic acid, dates to the mid 1800's and has continued to the present. Interest in polyaspartates and related molecules increased in the mid 1980's as awareness of the commercial potential of these molecules grew. Particular attention has been paid to biodegradable and environmentally compatible polyaspartates for commodity uses such as detergent additives and superabsorbent materials in disposable diapers, although numerous other uses have been contemplated, ranging from water-treatment additives for control of scale and corrosion to anti-tartar agents in toothpastes.

There have been some teachings of producing copolymers of succinimide and aspartic acid or aspartate via thermal polymerization of maleic acid plus ammonia or ammonia compounds. For example, U.S. Pat. No. 5,548,036 to Kroner et al. (1996) taught that polymerization at less than 140° C. resulted in aspartic acid residue-containing polysuccinimides. However, the reason that some aspartic acid residues persisted in the product polymers was that the temperatures of polymerization were too low to drive the reaction to completion, leading to inefficient processes.

JP 8277329 (1996) to Tomida exemplified the thermal polymerization of potassium aspartate in the presence of 5 mole % and 30 mole % phosphoric acid. The purpose of the phosphoric acid was stated, in the above patent, to serve as a catalyst so that molecules of higher molecular weight might be produced. However, the products of the reaction were of a lower molecular weight than were produced in the absence of the phosphoric acid, indicating that there was no catalytic effect. There was no mention of producing copolymers of aspartate and succinimide; rather, there was mention of producing only homopolymers of polyaspartate. In fact, addition of phosphoric acid in this fashion to form a slurry or intimate mixture with the powder of potassium aspartate, is actually counterproductive to formation of copolymers containing succinimide and aspartic acid residue units, or to formation of the condensation amide bonds of the polymers in general. That is, although the phosphoric acid may act to generate some fraction of residues as aspartic acid, it also results in the occurrence of substantial amounts of phosphate anion in the slurry of mixture. Upon drying to form the salt of the intimate mixture, such anions bind ionically with the positively charged amine groups of aspartic acid and aspartate residues, blocking them from the polymerization reaction, thus resulting in polymers of lower molecular weight in lower yield.

Earlier, U.S. Pat. No. 5,371,180 to Groth et al. (1994) had demonstrated production of copolymers of succinimide and aspartate by thermal treatment of maleic acid plus ammonium compounds in the presence of alkaline carbonates. The invention involved an alkaline, ring-opening environment of polymerization such that some of the polymeric succinimide residues would be converted to the ring-opened, aspartate form. For this reason, only alkaline carbonates were taught and there was no mention of cations functioning themselves in any way to prevent imide formation.

More recently, U.S. Pat. No. 5,936,121 to Gelosa et al. (1999) taught formation of oligomers (Mw<1000) of aspartate having chain-terminating residues of unsaturated dicarboxylic compounds such as maleic and acrylic acids. These aspartic-rich compounds were formed via thermal condensation of mixtures of sodium salts of maleic acid plus ammonium/sodium maleic salts that were dried from solutions of ammonium maleate to which NaOH had been added. They were producing compounds to sequester alkaline-earth metals. In addition, the compounds were shown to be nontoxic and biodegradable by virtue of their aspartic acid composition. Moreover, the compounds retained their biodegradability by virtue of their very low Mw, notwithstanding the presence of the chain-terminating residues, which when polymerized with themselves to sizes about the oligomeric size, resulted in non-degradable polymers.

A number of reports and patents in the area of polyaspartics (i.e., poly(aspartic acid) or polyaspartate), polysuccinimides, and their derivatives have appeared more recently. Notable among these, for example, there have been disclosures of novel superabsorbents (U.S. Pat. No. 5,955,549 to Chang and Swift, 1999; U.S. Pat. No. 6,027,804 to Chou et al., 2000), dye-leveling agents for textiles (U.S. Pat. No. 5,902,357 to Riegels et al., 1999), and solvent-free synthesis of sulfhydryl-containing corrosion and scale inhibitors (EP 0 980 883 to Oda, 2000). There also has been teaching of dye-transfer inhibitors prepared by nucleophilic addition of amino compounds to polysuccinimide suspended in water (U.S. Pat. No. 5,639,832 to Kroner et al., 1997), which reactions are inefficient due to the marked insolubility of polysuccinimide in water.

U.S. Pat. No. 5,981,691 to Sikes et al purportedly introduced the concept of mixed amide-imide, water-soluble copolymers of aspartate and succinimide for a variety of uses. The concept therein was that a monocationic salt of aspartate when formed into a dry mixture with aspartic acid could be thermally polymerized to produce the water-soluble copoly(aspartate, succinimide). The theory was that the aspartic acid comonomer when polymerized led to succinimide residues in the product polymer and the monosodium aspartate comonomer led to aspartate residues in the product polymer. It was not recognized that merely providing the comonomers was not sufficient to obtain true copolymers and that certain other conditions were necessary to avoid obtaining primarily mixtures of polyaspartate and polysuccinimide copolymers. In U.S. Pat. No. 5,981,691, the comonomeric mixtures were formed from an aqueous slurry of aspartic acid, adjusted to specific values of pH, followed by drying. There was no teaching of use of solutions of ammonium aspartate or any other decomposable cation plus NaOH, or other forms of sodium or other cations, for generation of comonomeric compositions of aspartic acid and salts of aspartate. Thus, although some of the U.S. Pat. No. 5,981,691 examples obtain products containing some copolymer in mixture with other products, particularly homopolymers, as discussed in the Summary of the Invention below, the theory that true copolymers could be obtained merely by providing the comonomers in the manner taught in U.S. Pat. No. 5,981,691 was not fully realized.

Thus, to date, there have been no successful disclosures of water-soluble or wettable, mixed amide/imide polyamino acids such as copolymers of aspartate and succinimide, related imide-containing polyamino acids, polysuccinimide or derivatives thereof.

SUMMARY OF THE INVENTION

One aspect of the invention relates to polymerizing aspartic acid to polysuccinimide in a supercritical fluid (SCF), such as liquid $CO_2$ or supercritical $CO_2$ in combination with an organic cosolvent. In another aspect of the present invention aspartic acid is polymerized in a supercritical fluid to form copoly(succinimide-aspartarte). In yet another aspect of the present invention the polysuccinimide or the copoly(succinimide-aspartate) formed in the supercritical fluid is derivatized to produce derivatives of the polysuccinimide and of the copoly(succinimide-aspartate). In another aspect of the present invention, catalysis is used for the polymerization and derivatization. In yet another aspect of the present invention, the polysuccinimide or the copoly (succinimide-aspartate) formed in a supercritical fluid are subsequently isolated and melt processed.

BRIEF DESCRIPTION OF THE DRAWING

FIG. 2C depicts the IR spectra of polysuccinimide synthesized in supercritical $CO_2$ at 200° C.. The appearance of the imide peak at 1714 $cm^{-1}$ is only in the higher temperature synthesis.

DESCRIPTION OF THE PREFERRED EMBODIMENTS

Figure 1:
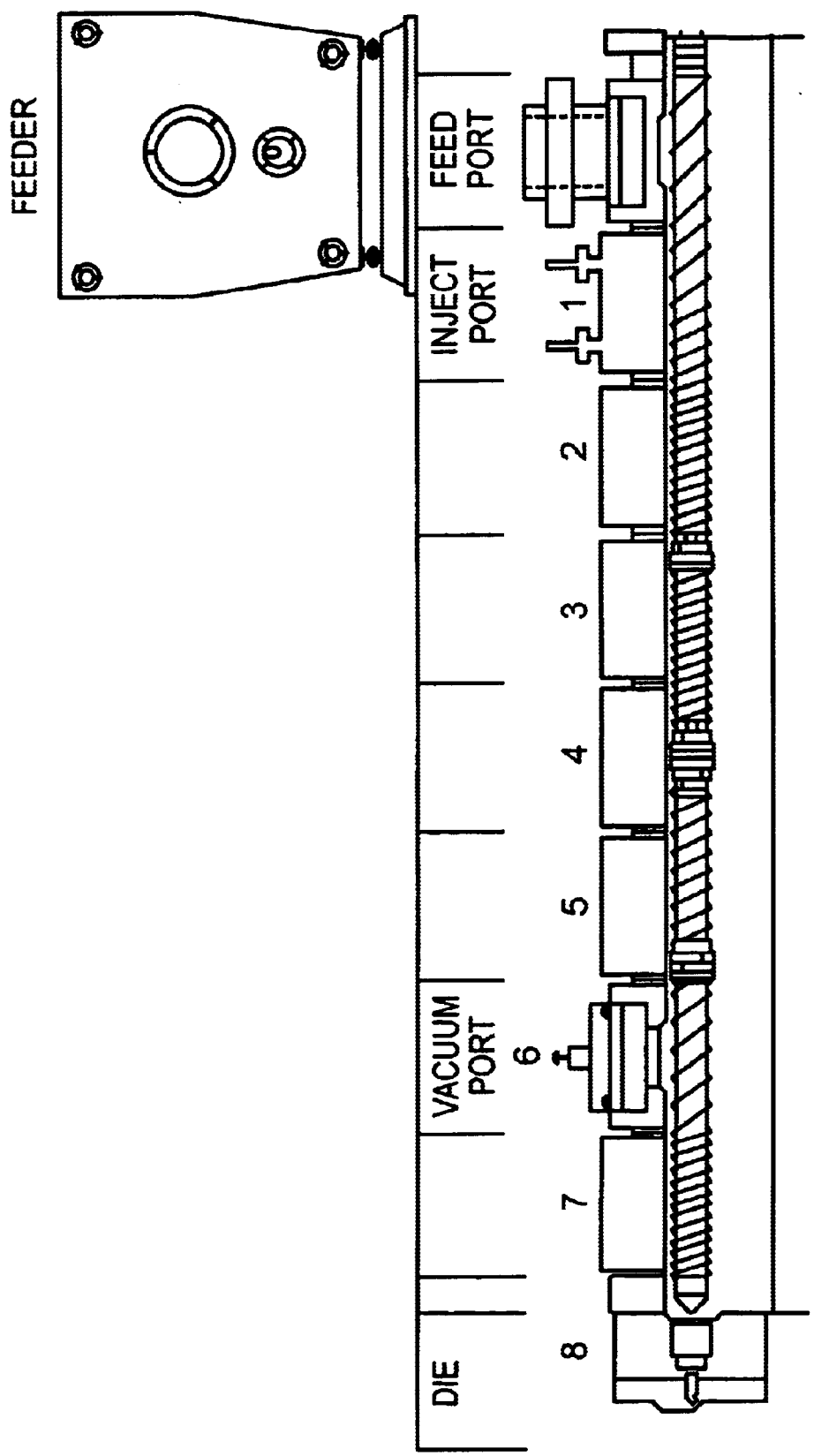
FIG. 1 depicts a diagram of a typical extrusion machine. The injection port allows the introduction of reactants into the injection machine for post reactions of the polymer or copolymers in the melt. The sections of the screw are separately heated and interchangeable. Thus, the injection port can be placed downstream in the injection machine depending on the required residence time required for a desired reaction.

These previous references fail to teach a method whereby a sufficiently intimate mixture of the comonomers is provided such that the polymerization leads to a true copolymer with a significant number of both aspartate and succinimide residues or the synthesis of polysuccinimide.

A. Thermal Synthesis of Copoly(Succinimide-Aspartate)

A method has now been discovered providing a sufficiently intimate mixture of the comonomers and, therefore, allowing the production of a true copolymer with a significant number of both aspartate (also referred to as amide) residues or units and succinimide (also referred to as imide) residues or units, as schematically shown by the following formula:

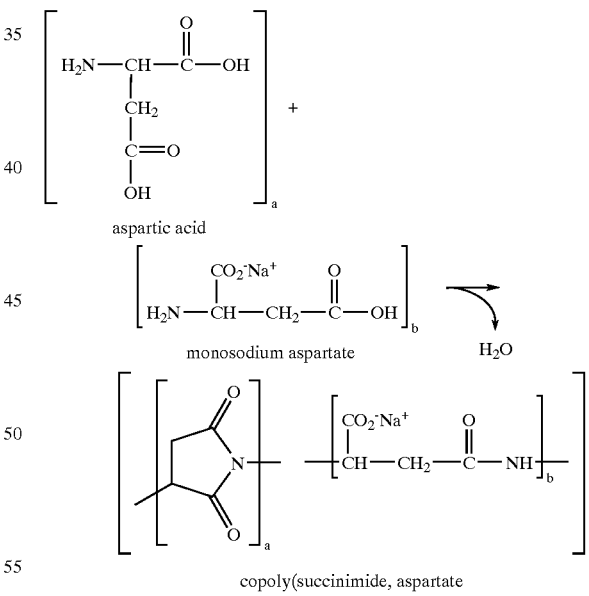

The invention also can provide the resulting copolymers in isolated form. By isolated form it is meant that the copolymer is either: (a) in the substantial absence, e.g., less than 10%, preferably less than 5%, more particularly less than 1%, by weight of a polyaspartate or polysuccinimide homopolymer, (b) prepared by a method defined by this invention or (c) polyaspartate and/or polysuccinimide homopolymer from the copolymer.

Accordingly, the present invention teaches novel methods for producing mixed amide/imide copolymers of amino acids, as well as the resulting novel imide-containing polyamino acids themselves. Included are methods employing the monomers aspartic acid or aspartate salts having non-volatile or non-heat-decomposable cations. By aspartate or aspartate salt is meant a salt of the aspartate ion and any metallic cation, including alkali metal, alkaline earth metals or transition metals. Preferably the cations are alkali or alkaline earth metals, particularly Na, Mg, K, Ca, Rb, Sr, Cs and Ba, with sodium, magnesium, potassium and calcium, particularly sodium, being preferred. These monomers lead to amide formation. Other amino acid monomers, particularly aspartates and lysine having a volatile or heat-decomposable cation, preferably an ammonium or amine cation, lead to imide formation. In the following, the amide-generating cation will be represented by sodium ($Na^+$) and the imide-generating cation will be represented by ammonium ($NH_4^+$) but with the understanding that other cations creating the same effects for achieving the invention may be substituted. By volatile or heat-decomposable cation it is meant that the cation sufficiently dissociates from the aspartate anion under the given drying conditions such that the remaining aspartate unit can cyclize to a succinimide unit during the polymerization. Cations which have at least 50% dissociation in this manner under the given drying conditions are considered volatile or heat-decomposable and cations which do not dissociate at least 50% are considered non-volatile or non-heat decomposable.

In the present invention, some elements of the conventional, enzymatic processes for production of L-aspartic acid can be adapted for producing monomers useful in the invention. The production of the comonomer mixture, however, is a novel aspect. The method involves providing an intimate solution of an aspartate of a non-volatile cation and an aspartate of a volatile cation. By the term aspartate is meant an aspartic acid residue, either as a monomer or as a polymerized or copolymerized unit having its carboxyl group in ionic form associated with a cation, i.e., as —$COO^-$. Specifically, for example, an ammonium aspartate solution can be titrated with NaOH to a fractional molar equivalence of a sodium salt of aspartate and an ammonium salt of aspartate. This comonomeric solution is then dried to produce a comonomer mixture of a partial sodium salt of aspartic acid and free aspartic acid. By free aspartic acid is meant aspartic acid or a polymerized or copolymerized aspartic acid residue having its carboxyl group not in ionic form, i.e., —COOH. Because the dried comonomer mixture is prepared from the novel intimate solution of comonomers, an intimate dried mixture of these comonomers is obtained. Although not intending to be bound by this theory, it is believed that the mixture is intimate to the extent of exhibiting a salt lattice structure of the aspartate with the aspartic acid. It is possible for the dried comonomeric composition to also contain some residual ammonium aspartate, but in very small amounts, e.g., not exceeding 5% by weight, preferably not exceeding 2% by weight.

In effect, the aspartate of the volatile cation (e.g. ammonium) when dried from aqueous solution, is largely converted to powdered or crystalline aspartic acid. This is due to the loss of the decomposable cation, e.g., ammonia, as a vapor upon drying, with accompanying lowering of the pH of the evaporating solution as ammonia leaves the solution, for example, as a result of the following equilibrium being pulled to the left:

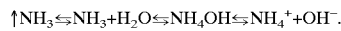

As is understood, however, by those skilled in the art, the term "dried" does not imply the complete absence of ammonia. Rather, the comonomer mixture might contain an amount of ammonia which is subsequently removed during the polymerization, as described below.

The sodium ion, on the other hand, has no significant vapor phase during drying and remains in the dried salt as a counter ion to aspartate monomers. Thus, the relative proportions of the comonomers, monosodium aspartate and aspartic acid, is set by the relative molar amounts of ammonium aspartate in solution and the NaOH added to the solution prior to drying.

The dried comonomer mixture is a clear, glassy solid at ambient temperatures if drying occurs in vacuo or in an oxygen-depleted atmosphere. In the presence of atmospheric oxygen, the dried comonomer preparation has a pale yellow, glassy appearance. At reaction temperatures it is a flowable viscous liquid.

The comonomer composition of the present invention may also be prepared via nonenzymatic, chemical production of solutions of ammonium aspartate. For example, maleic acid plus ammonia in water plus heating, preferably at an elevated pressure, may produce ammonium aspartate in solution. Typically, temperatures of 80 to 160° C., preferably 120 to 160° C. and a pressure of up to about 120 psi can be used, although other conditions may be useful depending on the particular circumstances. Upon addition of the desired amount of NaOH, this solution is dried to form the comonomer composition containing the mixture of the sodium aspartate salt and aspartic acid. Drying may be effected by any of the well known procedures, for example wipe film evaporators, drum driers, and rotary evaporators.

The comonomeric composition may also be obtained via coprecipitation from solution. For example, addition of a hydrophobe or downward adjustment of pH may lead to coprecipitation of the monomers. These may then be isolated, for example by filtration, for use in the production of the imide-containing polymers.

Also included are methods in which maleic acid plus ammonia plus soluble, nonalkali as well as alkali, cationic salts are used to internally generate a combination of aspartic acid and monosodium aspartate comonomers for thermal polymerization to produce water-soluble, imide containing copolymers.

B. Synthesis of Polysuccinimide (PSI) in a Supercritical Fluid

In another embodiment of the present invention a method has now been discovered allowing the production of polysuccinimide at high molecular weight and high yield in a supercritical fluid as a solvent. A supercritical fluid is a fluid medium that is at a temperature that is sufficiently high that it cannot be liquified by pressure. A supercritical fluid relates to dense gas solutions with enhanced solvation powers, and can include near supercritical fluids. The basis for a supercritical fluid is that at a critical temperature and pressure, the liquid and gas phases of a single substance can co-exist.

Further, supercritical fluids are unique states of matter existing above certain temperatures and pressures. As such, these fluids exhibit a high level of functionality and controllability that can influence not only the macrophysical properties of the fluid, but also influence nano-structures of molecules dissolved in them.

The supercritical fluid phenomenon is documented, for example, in the *CRC Handbook of Chemistry and Physics*, 67th Edition, pages F-62 to F-64 (1986–1987), published by the CRC Press, Inc., Boca Raton, Fla. At high pressures above the critical point, the resulting supercritical fluid, or "dense gas", attains densities approaching those of a liquid and assumes some of the properties of a liquid. These properties are dependent upon the fluid composition, temperature, and pressure. As used herein, the term "critical point" denotes the transition point at which the liquid and gaseous states of a substance merge with each other and represents the combination of the critical temperature and critical pressure for a given substance.

The compressibility of supercritical fluids is great just above the critical temperature where small changes in pressure result in large changes in the density of the supercritical fluid. The "liquid-like" behavior of a supercritical fluid at higher pressures results in greatly enhanced solubilizing capabilities compared to those of the "subcritical" compound, with higher diffusion coefficients and an extended useful temperature range compared to liquids. It has also been observed that as the pressure increases in a supercritical fluid, the solubility of the solute often increases by many orders of magnitude with only a small pressure increase.

Near-supercritical liquids also demonstrate solubility characteristics and other pertinent properties similar to those of supercritical fluids. Fluid "modifiers" can often alter supercritical fluid properties significantly, even in relatively low concentrations. In one embodiment, a fluid modifier is added to the supercritical fluid. These variations are considered to be within the concept of a supercritical fluid as used in the context of this invention. Therefore, as used herein, the phrase "supercritical fluid" also denotes a compound above, at, or slightly below the critical temperature and pressure (the critical point) of that compound.

The use of supercritical fluids in the production of polymers as a swelling, foaming or purification agent is known from various sources. Supercritical fluid serves to increase resin mobility thereby improving mixing and processing, to reduce the polymer glass transition temperature by swelling, and enabling processing at lower temperatures, and acts as a solvent for impurities (including unreacted monomer and residual conventional solvents) which may be removed during the processing to give high purity products. Moreover the fluid can be used to aerate the polymer by transition to non critical gaseous state whereby a porous material may be obtained. Supercritical fluid has found application in incorporation of dyes and other inorganic materials which are insoluble in the supercritical fluid, for example inorganic carbonates and oxides, into polymers with a good dispersion to improve quality, in particular dispersion in products such as paints for spray coating and the like.

Accordingly, in another embodiment of the present invention an additive is dispersed into the polysuccinimide or copoly(succinimide-aspartate) or a derivative thereof formed in a supercritical fluid.

Examples of compounds which are known to have utility as supercritical fluids are, but are not limited to, $CO_2$, $NH_3$, $H_2O$, $N_2O$, xenon, krypton, methane, ethane, ethylene, propane, pentane, methanol, ethanol, isopropanol, isobutanol, $CClF_3$, $CFH_3$, cyclohexanol, $CS_2$ and a mixture thereof.

Due to the low cost, environmental acceptability, non-flammability, and low critical temperature of carbon dioxide, nitrous oxide, and water, supercritical carbon dioxide, nitrous oxide and/or $H_2O$ fluid is preferably employed in the present invention. More preferably carbon dioxide is employed in the present invention.

In another embodiment of the present invention, a cosolvent is preferably used in conjunction with the supercritical fluid as a polymerization vehicle. Suitable cosolvents include, but are not limited to, trans-2-hexenyl acetate, ethyl trans-3-hexenoate, methyl caproate, isobutyl isobutyrate, butyl acetate, butyl methacrylate, hexyl acetate, butyl butyrate, pentyl propionate, methyl ethanoate, ethyl caproate, methyl dodecanoate, 2-ethylbutyl acetate, methyl oleate, dodecyl acetate, methyl tridecanoate, soybean oil methyl esters, hexane, heptane, tetradecane, hexadecane, toluene, 1-hexadecene, ethanol, methanol, propanol, 1-dodecanol, 1-nonanol and a mixture thereof.

The supercritical fluid is preferably maintained at a pressure from about 500 psi to about 2500 psi, more preferably from about 700 psi to about 2000 psi, and at a temperature from about 50° C. to about 300° C., more preferably from about 100° C. to about 250° C. The term "about" is used in the present application to denote a variation of 10% of the stated value.

The weight percentage of cosolvent and solute in the supercritical fluid is preferably from about 1% to about 20%, more preferably from about 5% to about 15%.

The weight average molecular weight of the polysuccinimide in accordance with the above process is in the order of from about 2,000 to about 10,000 Dalton, including all increments within that range, and preferably in the order of from about 3,000 to about 5,000 Daltons.

In another embodiment of the present invention the polymerization of aspartic acid to polysuccinimide in a supercritical fluid is carried out in the presence of a catalyst, preferably an acidic catalyst, such as phosphoric acid and polyphosphoric acid. In this embodiment a weight average molecular weight of up to several hundred thousand Daltons is obtained, preferably up to 300,000 Daltons, preferably up to 200,000 Daltons and any increments within this range.

In another embodiment of the present invention, the polymerization is carried out in the presence of a thermal stabilizer or an antioxidant or a mixture thereof.

In an additional embodiment of the present invention, the polymerization of aspartic acid is performed in the dispersed phase. The term "dispersed phase" is herein used to denote a heterogeneous mixture where the monomer particles are suspended in the polymerization medium, where the polymerization medium forms the continuous phase.

In accordance with the present invention, the product of the polymerization is isolated by concentrating the polymerization medium, in particular water, by a method such as: distillation, screw extrusion, thin film evaporation, drum evaporation, by means of a belt dryer, spray drying, or evaporation of the supercritical fluid by subjecting the supercritical fluid to suitable collection port under reducing pressure.

C. Synthesis of Copoly(Succinimide-Aspartate) in a Supercritical Fluid

In another embodiment of the present invention a copoly (succinimide-aspartate) is synthesized in a supercritical fluid at high molecular weight and high yield. In accordance with this embodiment, a mixture of sodium aspartate and ammonium aspartate is prepared in a similar manner to that discussed in the thermal synthesis of copoly(succinimide-aspartate) above. This mixture is then subjected to polymerization in a supercritical fluid in a method similar to that described for the synthesis of polysuccinimide above. The weight average molecular weight is in the order of about 1,000 to about 100,000 Dalton, including all increments within that range, and preferably in the order of from 3,000 to 10,000 Daltons.

In another embodiment the above polymerization is carried out in the presence of a catalyst, preferably an acid catalyst such as phosphoric acid or polyphosphoric acid. In this embodiment the copoly(succinimide-aspartate) formed exhibits a weight average molecular weight of up to several hundred thousand, preferably up to 300,000 Daltons.

In an additional embodiment in accordance with the present invention, the polymerization is carried out in the presence of a thermal stabilizer or an antioxidant or a mixture thereof.

Additional comonomers may be added prior to the drying of the comonomer solution step to provide comonomeric feedstock for terpolymers and high polymers of thermally condensed polyamino acids. In particular, the amino acids lysine and glutamate and salts thereof may be used. These can impart further water-solubility to the product imide-containing polymers. Moreover, other difunctional and multifunctional monomers such as aminocaproic acid and ornithine, as well as the other common amino acids including but not limited to alanine, glycine, leucine, isoleucine, methionine which can form a sulfoxide by oxidation of the thioether, and theronine; sugar-acids such as glucuronic acid; other hydroxyl-containing carboxylates such as citric acid and malonic acids; and other like molecules, are additional comonomers that would co-condense in the production of the imide-containing polyamino acids and may be useful to provide aqueous solubility and other useful properties to the imide-containing polyamino acids.

Additional preferred comonomers include, but are not limited to caprolactam; caprolactone; glutamine; arginine; asparagine, which is inherently present in the product, in accordance with the present invention, in an amount of from 0 to 15%; and cystine, which preferably forms a disulfide which can be further subjected to reductive cleavage to yield two mercaptans, which mercaptans are available for further derivatization or oxidative cleavage to form a sulfonate. Further, additional comonomers include, but are not limited, an aminosugar, glutamine, and chitin, chitosan, at a weight average molecular weight ranging from an oligomer to 1,000,000 including all increments within the above range. Further comonomers include but are not limited to, a polysaccharide ranging in weight average molecular weight from that of an oligomer to that of a naturally occurring polysaccharide, including all increments within the above range. The term "oligomer" as used in the present application denotes a resin with a degree of polymerization (DP) between 10 and 1000.

D. Ring-opening of Polysuccinimide to Form a Derivative in a Supercritical Fluid The term "ring-opening" as used in this application denotes the formation of a derivative of polysuccinimide by opening at least one succinimide ring, as shown schematically by the following reaction:

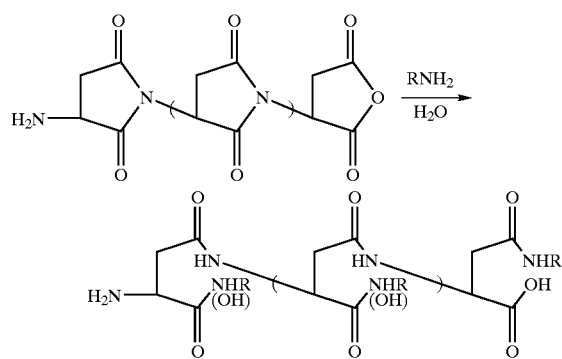

In one embodiment, in accordance with the present invention, the polysuccinimide formed in a supercritical fluid undergoes ring-opening, prior to isolation from the supercritical fluid, to form a derivative.

Until now derivatives such as those made from copoly (succinimide-aspartate) have been very difficult to make. We have discovered that polysuccinimide can be derivatized by using combinations of amines. For example, a combination of ammonium hydroxide and 2-aminoethanol resulted in the formation of a resin with free carboxylic acid salts, and the amides of ammonia and aminoethanol. Additional compounds in accordance with the present invention include aminopyridine and imidazole.

It is sometimes preferable to have the polysuccinimide substantially in the absence of sodium salts. The usual salts derived from polysuccinimide hydrolysis with sodium hydroxide result in the sodium polyaspartate. Thus, in another aspect of this invention the succinimide rings are hydrolyzed by a tertiary amine to form the tertiary amine salt of polyaspartic acid.

An amine in accordance with the present invention is any amine of the general formula:

$$R_1R_2R_3N$$

where $R_1$, $R_2$, and $R_3$ are the same or different radicals selected from a hydrogen, an alkyl, such as methyl, ethyl, n-propyl, isopropyl, n-butyl, isobutyl, sec-butyl, t-butyl, n-amyl, isoamyl, t-amyl, n-hexyl, n-octyl, capril, n-decyl, lauryl, myristyl, cetyl, and stearyl; substituted alkyl, such as hydroxyethyl; alkenyl, such as allyl; aryl, such as phenyl; aryl-alkyl, such as benzyl; or substitute aryl radical, such as alkylphenyl, chlorophenyl and nitrophenyl.

Further, a polyamine, such as a diamine, a triamine, a protein, a peptide, a gelatin, chitin, lysine, ornithine, or a melamine, can be used to provide additional sites for further reactions. An example of the latter is to open the succinimide ring with an aminoalcohol, such as a diethanolamine, to provide a polyfunctional OH group-containing resin to further react. A further example is to open all the succinimide rings with sufficient diamine, such as hexamethylene diamine, so that no crosslinking can occur but that each amide formed has an amine group at the end. Thus, chemistry can be performed on that amine group, such as a reaction with a polyfunctional isocyanate to chain extend the imide-containing polyamino acid or to form a crosslinked gel. An aminoethoxylate can be used to form a polymer with a long chain ethoxylate. Also, an aminoethoxylate containing a hydrophobic end group can be used to form a rheology modifier or an associative thickener. An additional amino functional material can be used to react in a nucleophilic addition with the imide-containing polyamino acid such as: an allyl. Further, amino polybutadiene and an amino terminated fatty olefin can be used in a nucleophilic addition with the imide-containing polyamino acid which could achieve the same result as an allyl amine and in addition be able to crosslink by an oxidative cure mechanism. Further, an amino-aromatic compound, such as aniline or a substituted aniline can be used in the nucleophilic addition in accordance with the present invention. Preferably, the amine is tertiary amine, more preferably, triethanol amine.

Therefore by the proper combination of various amines, derivatives can be made from polysuccinimide which are similar in functionality to those made from copoly (succinimide-aspartate) but exhibit higher molecular weight and reduced color.

The ring-opening reactions in accordance with the present invention can be carried out either in a supercritical fluid (SCF) or in water.

In another embodiment of the present invention, the polymerization is carried out in the presence of a thermal stabilizer or an antioxidant or a mixture thereof as discussed below.

E. End-Capping Polymerization in a Supercritical Fluid

In a further embodiment of the present invention a polymer or copolymer containing succinimide moieties is formed in a supercritical fluid by end-capping polymerization. The term "end-capping" is used in the present application to denote the initiation of chain growth polymerization by using an anhydride, such as succinic anhydride, as shown in Reaction 1 below, succinic acid, as shown in Reaction 2 below or an amine, as shown in Reaction 3 below:

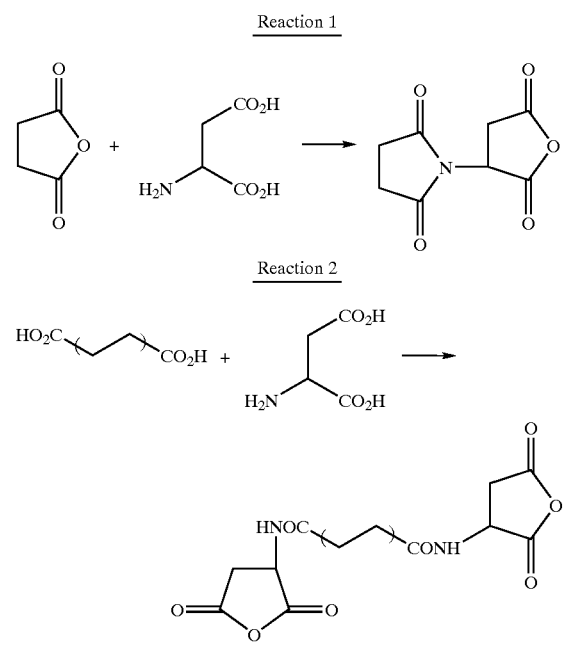

Thus, the anhydride reacts with the amino group of the L-aspartic acid to form an amide bond which then cyclizes to form the succinimide moiety. Meanwhile the carboxyl group of the L-aspartic acid reacts with the amino group of another L-aspartic acid, to build up the chain length, and then cyclizes. This proceeds until the L-aspartic acid is used up. The final L-aspartic acid carboxyl groups cyclize to form the anhydride.

Suitable end-capping initiators used to initiate polymerizations and contain chosen end groups in accordance with the present invention, include but are not limited to, an anhydride such as succinic anhydride; phthalic anhydride; maleic anhydride; alkenyl succinic anhydride, which leaves a hydrocarbon chain with a double bond; 1,2,4-benzenetricarboxylic anhydride; cis-1,2,3,6-tetrahydrophthalic anhydride; 1,2-cyclohexane dicarboxylic anhydride; or a carboxylic acid, such as benzoic acid; thiolsuccinic acid, which would leave a thiol end group; and terephthalic acid. From the known concentration of the initiator the molecular weight of the chain, that is the chain length, can be controlled by controlling the amount of aspartic acid used.

In another embodiment of the present application the end-capping initiator is an amine, as shown in Reaction 3 below:

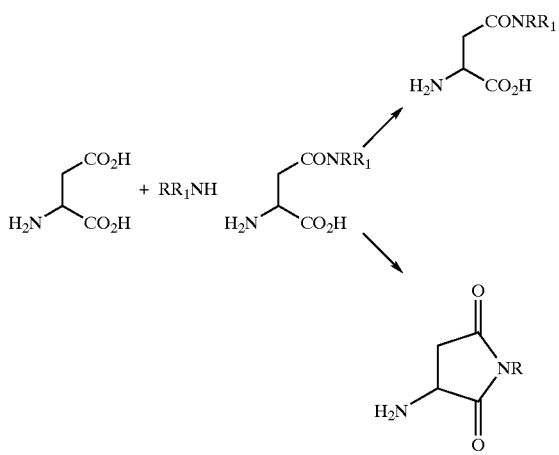

where R, and $R_1$, are the same or different radicals selected from an alkyl, such as methyl, ethyl, n-propyl, isopropyl, n-butyl, isobutyl, sec-butyl, n-amyl, isoamyl, n-hexyl, n-octyl, capril, n-decyl, lauryl, myristyl, cetyl, and stearyl; substituted alkyl, such as hydroxyethyl; alkenyl, such as allyl; aryl, such as phenyl; aryl-alkyl, such as benzyl; or substitute aryl radical, such as alkylphenyl, chlorophenyl and nitrophenyl.

Accordingly, suitable end-capping initiators containing an amine group which reacts with the carboxilic group of the L-aspartic acid include, but are not limited to, an aliphatic amine, such as methylamine, dimethylamine, trimethylamine, ethylamine, diethylamine, n-propylamine, di-n-propylamine, n-butylamine, n-amylamine, n-hexylamine, laurylamine; an aliphatic diamine, such as ethylenediamine, trimethylenediamine, tetramethylenediamine, pentamethylenediamine, hexamethylenediamine; an aliphatic hydroxylamine, such as ethanolamine, diethanolamine, triethanolamine; an aromatic amine, such as aniline, methylaniline, dimethylaniline, diethylaniline, o-toluidine, m-toluidine, p-toluidine; and an aromatic diamine, such as o-phenylenediamine, m-phenylenediamine, p-phenylenediamine.

In a further embodiment the anhydride end group is reacted with an aminoethoxylate, hydrophobic amine, or hydroxyl terminated materials. Additional suitable nucleophiles include, but are not limited to, a poly(vinyl alcohol); a polyester; a polyamide; a polysaccharide, such as starch; a dextan; and a cellulose; a protein; a dye; and a UV absorber. The anhydride reacts considerably faster than the succinimide moieties within the chain.

Thus, in an embodiment in accordance with the present invention, the polymer formed by end-capping initiation contains a specific chain end functionality, introduced to the polymer by the choice of the end-capping initiator.

In another embodiment the polymerization in the presence of the end-capping initiator is carried out in a solvent, such as water, or in a supercritical fluid, or in the molten phase or in the solid phase.

In another embodiment of the present invention a prepolymer is formed. The term "prepolymer" is used herein to denote a polymer with low molecular weight, preferably from 100 to 1,000 weight average molecular weight. Subsequently the polymerization proceeds in the absence of the end-capping initiator as described above in the thermal and supercritical fluid polymerizations, or in the molten phase or in the solid phase.

An advantage of this approach is that the end-capping reaction improves significantly the color of the final product. Although Applicants do not wish to be bound to any theories, they believe that this is due to the fact that the process is not on the basic side and the amine groups are tied up rapidly. Interestingly, it has been found that the color gets better as the ratio of the end-capping chain initiator (CI) to L-Aspartic Acid (AA), CI:AA, increases from 1:1 to 1:10, preferably from 1:1 to 1:5.

In another embodiment by properly controlling the ratio of CI:AA discussed above as well as the chain initiating group a material is formed in the molten state at the reaction temperature which is amenable to processing via extrusion, as described below.

Another advantage lies in the anhydride end of the chain in that further reaction can be initiated from that end. For example, other monomers can be used to build chains exhibiting greater flexibility, hydrophobicity or a specific hydrophobic/hydrophilic value. In one of the embodiments a block copolymer is formed in this manner.

In another embodiment in accordance with the present invention an oligomer is formed in an extruder and subsequently an additional monomer or mixture of monomers is introduced in the extruder through an injection port as shown in FIG. 1. One can envision the preparation of numerous products, with controlled weight average molecular weight ranging from 1,000 to 150,000, including all increments within that range, preferably, from 1,000 to 10,000 Daltons, in one continuous process.

In another embodiment, a copolymer formed by the end-capping initiation of the present invention is derivatized by reacting a nucleophile with a succinimide ring. In this process an end-capped oligomer is formed, which subsequently is chain extended and finally derivatized to form a final product. The entire process is preferably carried out in an extruder.

Additional suitable monomers which can be used to chain extend, besides L-aspartic acid, include but are not limited to, amino acids, hydroxy acids, and combinations of a diamine or a diol with a dicarboxylate to form a polyamide or a polyester.

Additional comonomers described above under the thermal processing may also be used in accordance with this embodiment.

In another embodiment the end-capping initiator contains an amine group which reacts with the carboxilic group of the L-aspartic acid. Such amine end-capping initiators include, but are not limited to, an aliphatic amine, such as methylamine, dimethylamine, trimethylamine, ethylamine, diethylamine, triethylamine, n-propylamine, di-n-propylamine, tri-n-propylamine, n-butylamine, n-amylamine, n-hexylamine, laurylamine; an aliphatic diamine, such as ethylenediamine, trimethylenediamine, tetramethylenediamine, pentamethylenediamine, hexamethylenediamine; an aliphatic hydroxylamine, such as ethanolamine, diethanolamine, triethanolamine, aminoethoxylate; an aromatic amine, such as aniline, methylaniline, dimethylaniline, diethylaniline, o-toluidine, m-toluidine, p-toluidine; and an aromatic diamine, such as o-phenylenediamine, m-phenylenediamine, p-phenylenediamine.

In a further embodiment the anhydride end group is reacted with an aminoethoxylate, hydrophobic amine, or hydroxyl terminated materials. Additional suitable nucleophiles include, but are not limited to, a poly(vinyl alcohol); a polyester; a polyamide; a polysaccharide, such as starch; a dextan; and a cellulose; a protein; a dye; and a UV absorber. The anhydride reacts considerably faster than the succinimide moieties within the chain.

In an additional embodiment the succinimide moieties react with aminoethoxylate, hydrophobic amine, or hydroxyl terminated materials to form a graft copolymer, such as a comb-graft copolymer.

Proper control of the molecular weight and the functionalities result in dispersants, surface active agents, rheology modifiers, thickeners, corrosion inhibitors, sun screens, gels in water or in solvents, etc.

Preferably the end-capping reaction is carried out in the presence of a catalyst. Suitable catalysts include, but are not limited to, a protonic acid, such as polyphosphoric acid; a Lewis acid; an organometallic catalyst, preferably one of those used for condensation reactions, such as tin octanoate.

In another embodiment of the present invention the end-capping reaction is initiated via the amino group in the presence of a primary or secondary amine.

In another embodiment the resin formed in accordance with the present invention is stabilized with polymer additives before or after isolation. Polymer additives are discussed in the *Modern Plastics Encyclopedia*, A Division of McGraw Hill Companies, 72, pages C-3 to C-117 (1995) and in Kirk-Othmer *Concise Encyclopedia of Chemical Technology*, John Wiley & Sons, New York, pages 129–130 (1985), both of which are incorporated herein by reference.

In another embodiment of the present invention, the preparation of a derivative in accordance with the present invention is carried out in the presence of a thermal stabilizer or an antioxidant or a mixture thereof as discussed below.

F. Polymer Additives

The polymers of the present invention may be mixed with a number of additives during the polymerization, prior to isolation, as described above, or post isolation (compounding). The additives are selected to impart the desired properties to the end product and to facilitate its fabrication. In the post isolation mixing (compounding) of additives, it is preferred that the polymers, copolymer or derivatives of the present invention are blended with a material to reduce the melt viscosity of the polymers, copolymer or derivatives of the present invention. Such materials include, but are not limited to, a plasticizer or a polymer, other than the polymers in accordance with the present invention, to form a polymer blend; preferably the resulting polymer blend is substantially a miscible polymer blend. Arriving at a specific complex formulation may be the result of an engineering art and experimentation. Preferred polymer additives include, but are not limited to the following:

Stabilizers: During processing a polymer must be brought to the molten state at temperatures much above those of their melting or glass transition. This is done to lower their viscosity and to extend the upper limit of possible processing rates without melt fracture. Consequently there is the real danger of thermal degradation during processing. For this reason heat stabilizers, such as free radical scavengers, maybe used. Polymer chains maybe also sensitive to forms of energy other than thermal. In particular, uses that are intended for outdoor applications must be able to withstand ultraviolet (UV) radiation, for which purpose UV stabilizers are added. In addition the polymer maybe stabilized against oxidative degradation, both short term at elevated processing temperatures, and long term during storage and use. In an oxidative degradation oxygen is absorbed and produces free radicals that react with the chains, usually autocatalytically, and degrade them. Most of the antioxidants combine with the oxygen-generated free radicals and inactivate them.

Antioxidants: Antioxidants are chemical compounds which are incorporated at low concentrations into polymer systems to retard or inhibit polymer oxidation and its resulting degradative effects by atmospheric oxygen. Their use is essential in order to protect the polymer during production, processing, compounding, and end use. Oxidation is a common natural phenomenon which can occur at any phase of a polymer's existence: during polymerization, processing, or end use of the product. The process may cause a variety of chemical and physical changes such as discoloration, loss of gloss or transparency, surface chalking and cracks. Oxidation tends to lower the physical properties of a polymer, such as impact strength, elongation, and tensile strength. The process may continue to degrade a polymer article until it loses its utility. The rate and effects of oxidation differ depending on the polymer, manufacturing process, and morphology.

Auto-oxidation: Organic materials react with molecular oxygen in a process called "auto-oxidation". Auto-oxidation is a free-radical chain reaction and, therefore, can be inhibited at the initiation and propagation steps. The process is initiated when free alkyl radicals (R.) are generated in the polymer by heat, radiation, stress, or residues. Without the protection afforded by antioxidants, these radicals begin a chain reaction which degrades the polymer.

Although Applicants do not wish to be bound to any particular theory, it is generally believed that polymeric oxidation begins when a free radical containing a highly reactive electron reacts with oxygen forming peroxy radicals (ROO.). These react with the polymer to produce hydroperoxides (ROOH) which decompose further to form two new free radicals. These begin the cycle anew, propagating a cascade of reactions that, sometimes in the absence of an antioxidant, can turn into a chain reaction leading to the failure of the polymer. Antioxidants terminate this sequence and eliminate free radicals from the system.

Stabilization is achieved either by termination reactions or by inhibiting the formation of free radicals. Primary antioxidants increase the number of terminations while secondary antioxidants reduce the formation of free radicals. Primary and secondary antioxidants are often used together with synergistic results.

Primary antioxidants: Primary antioxidants such as hindered phenols and secondary arylamides interrupt free radical processes by donating labile hydrogen atoms to change propagating hydroperoxy radicals into stable species.

Hindered phenols: Hindered phenols interrupt the auto-oxidation cycle. The hindered phenol is capable of donating hydrogen atoms, undergoing rearrangement reactions, and further reacting with free radicals until it is fully consumed. Over-oxidation of the hindered phenol is undesirable since it causes discoloration. Several approaches to stabilization which avoid over-oxidation of the phenolic have been developed. Trivalent phosphorous compounds and antacids (calcium stearate and zinc stearate) to scavenge acidic catalyst residues are typically used as co-additives in combination with the phenolic. Most of the newer commercial antioxidants are of this type, such as alkylated hydroquinones and phenols. In high temperature applications, polynuclear phenols generally are preferred over monophenols because of their lower sublimation rates. Phenolic antioxidants are typically used at levels ranging from 0.05 to 2.0 wt %.

Amines: The ability of amines, preferably aromatic amines, to stabilize at high temperature makes them useful in applications requiring prolonged exposure to elevated temperatures. Amines can be classified further as ketone-amine condensation products, diaryldiamines, diarylamines, and ketone-diarylamine condensation products. Both solid and liquid products are marketed. Typical use levels are 0.5 to 3%.

Secondary antioxidants: Secondary antioxidants, such as phosphites or thioesters, are peroxide decomposers that undergo redox reactions with hydroperoxides to form stable products. They are cost effective because they can be substituted for a portion of the more costly primary antioxidant and provide equivalent performance.

Phosphites: Phosphites generally are used in combination with other antioxidants, particularly phenols, the most commonly used secondary antioxidants, reduce hydroperoxides to alcohols. Phosphites are highly effective process stabilizers, nondiscoloring, and have broad FDA regulation for many indirect food contact applications. Tri (mixed nonyl- and dinonylphenyl) phosphite is used in the largest volume. Use levels vary from 0.05 to 3.0 wt %.

Thioesters: Thioesters reduce hydroperoxides to alcohols. Thioesters are nondiscoloring, FDA regulated, and incorporated to improve long-term heat stability. Typical use levels are from 0.1 to 0.3 wt % in polyolefins with higher levels used in polymers containing unsaturation.

Synergy between primary and secondary antioxidants: Combinations of certain antioxidants sometimes provide synergistic protection. The most common synergistic combinations are mixtures of antioxidants operating by different mechanisms. For example, combinations of peroxide decomposers may be used with propagation inhibitors. Similarly, combinations of metal chelating agents maybe used with propagation inhibitors. Synergistic combinations of structurally similar antioxidants are also known, particularly combinations of phenols.

Blends of a phenolic and a phosphite are very useful for melt compounding. They work well to maintain the molecular weight of the polymer, while at the same time maintaining low color. The phosphite decomposes hydroperoxides and protects the phenolic during processing thereby preventing (if optimum levels of both are added) over-oxidation of the hindered phenol and inhibiting the formation of colored by-products. This preserves the phenolic for long term thermal stability. Blends of the phenolic antioxidant and a thioester are a good combination for long term thermal stability of the polymer.

Two main classes of antioxidants inhibit the initiation step in thermal auto-oxidation. The peroxide decomposers function by decomposing hydroperoxides through polar reactions. Metal deactivators are strong metal-ion complexing agents that inhibit catalyzed initiation through reduction and oxidation of hydroperoxides. The most important commercial propagation inhibitors are hindered phenols and secondary alkylaryl- and diarylamines.

Additional antioxidants include:

Sulfides: Dilauryl thiodipropionate and distearyl thiodipropionate are the most important commercial antioxidants in this class. They are used with phenols to give synergistic combinations.

Metal salts of dithioacids: These substances act as hydroperoxide decomposers and propagation inhibitors, and are used in conjunction with other antioxidants, particularly phenols.

Bound antioxidants: Recently, antioxidants have been developed that are copolymerized into the polymer chain. The main advantage of such a system is low antioxidant extractability in applications where the polymer is in contact with solvents capable of extracting conventional antioxidants.

Additional Additives Include:

Colorants: Preferably, for decorative reasons, colorants such as pigments and dyes that absorb light at specific wavelengths are added to the polymers of the present invention.

Plasticizers: The term "plasticizer" stems from the process of making the polymer more susceptible to plastic flow.

Plasticizers, preferably external plasticizers, are usually monomeric molecules that when mixed with polar or hydrogen bonded polymers, position themselves between these intermolecular bonds and increase the spacing between adjacent bonds. Of course they must also either be polar or be able to form hydrogen bonds. The result of this action is to lower the level of the strength of intermolecular forces, thus decreasing the mechanical strength and increasing the flexibility of the rigid structure. The plasticizer may preferably be introduced to the polymer by copolymerization. In this context copolymerization is sometimes referred to as internal plasticization.

Reinforcing Agents: This category of additives is very broad and yet very important in that such additives improve the mechanical properties of the base polymers, chiefly their strength and stiffness. Short and long glass fibers, graphite fiber are common additives in applications calling for improved mechanical properties, including the absence of creep (dimensional stability). Solid reinforcing agents also extend the upper temperature limit of the use of the base polymer.

Fillers: The main function of fillers is to reduce the cost of the end product. A very inexpensive filler, occupying a fraction of the volume of a plastic article, will have such an economic benefit. Nevertheless, fillers are also often specialty additives; they may be present to reduce the thermal expansion coefficient of the base polymer, to improve its dielectric properties, or to "soften" the polymers (e.g., calcium carbonate).

Lubricants: Lubricants are very low concentration additives that are mixed with polymers to facilitate their flow behavior during processing. There are two categories of lubricant, external and internal. External lubricants are incompatible at all temperatures with the polymer they are used with; therefore during processing they migrate to the melt-metal interface, promoting some effective slippage of the melt by reducing interfacial layer viscosity. Internal lubricants, on the other hand, are polymer compatible at processing temperatures, but incompatible at the use temperature. Therefore, during processing they reduce chain-to-chain intermolecular forces, thus melt viscosity. As the processed plastic products cool, they become incompatible (phase separation) and can eventually migrate to the surface; thus product properties are not permanently affected.

In an additional embodiment in accordance with the present invention, the polysuccinimide, a copolymer or a derivative thereof is processed in a processing equipment. The processing of polymers is discussed extensively in *Principles of Polymer Processing* by R. T. Fenner, Chemical publishing (1979) and *Principles of Polymer Processing*, by Z. Tadmor et al, John Wiley & Sons, New York, (1979) both of which are incorporated herein by reference. Following are some aspect concerning the processing of the materials of the present invention:

G. Processing

The materials of the present invention can be further processed by one of the principal methods used to process thermoplastic materials into finished or semi-finished products, namely, screw extrusion, injection molding, blow molding and calendering. An important distinction exists between extrusion and calendering on the one hand, and molding techniques on the other, in that while the former are continuous processes, the latter are discontinuous. The term "materials of the present invention" is used to denote polysuccinimide, copoly(succinimide-aspartate), a derivative thereof and a blend thereof with an additive.

Screw Extrusion: In an embodiment in accordance with the present invention the materials of the present invention are extruded. The extrusion process is used to shape a molten polymeric material into a desired form by forcing it through a die. A variety of profiles can be formed in a continuous extrusion which include, but are not limited to, filaments, films and sheets. The required pressure is generated by at least one rotating screw in a heated barrel as shown in FIG. 1. While the form of the die determines the initial shape of the extrudate, its dimensions may be further modified, for example, by stretching, before final cooling and solidification takes place. A screw extruder may also be used, in accordance with the present invention, to further react the polyimide of the present invention by means of introducing a reactant in the extruder through an injection port as shown in the Figure. The segments of the Extruder can be separately heated to different temperatures. Further, the position of the injection port can be moved to a different location along the screw of the extruder to facilitate different residence time and reaction time of the reactant within the extruder. It is also possible to add additional injection ports to facilitate the addition of different reactants that require different residence time in the extruder in order to facilitate to desired reaction.

Single-screw Extrusion: The Figure shows the diagrammatic cross-section of a typical single-screw extruder, which is used to melt and to pump the polymer. Solid material in the form of either granules or powder is usually gravity fed through the hopper, although crammer-feeding devices are sometimes used to increase feed rates. The channel is relatively deep in the feed section, the main functions of which are to convey and compound the solids. Melting occurs as a result of the supply of heat from the barrel and mechanical work from the rotation of the screw.

The screw is held in position by an axial thrust bearing and driven by an electric motor via a reduction gearbox. Screw speeds are generally within the range of from 50 to 150 revolutions/minute, and it is usually possible to vary the speed of a particular machine over at least part of this range.

Barrel and die temperatures are maintained by externally mounted heaters, typically of the electrical-resistance type. Individual heaters or groups of heaters are controlled independently via thermocouples sensing the metal temperatures, and different zones of the barrel and die are often controlled at different temperatures. The region of the barrel around the feed pocket is usually water cooled to prevent fusion of the polymer feedstock before it enters the screw channels. Cooling may also be applied to part or all of the screw by passing water or other coolant through a passage at its center, access being via a rotary union on the driven end of the screw.

The size of an extruder is defined by the nominal internal diameter of the barrel. Sizes range from about 25 mm for a laboratory machine, through 60–150 mm for most commercial product extrusions, up to 300 mm or more for homogenization during polymer manufacture. Common thermoplastic extruders have screw length-to-diameter ratios of the order of 25 or more. An important characteristic of a screw is its compression ratio, one definition for which is the ratio between channel depths in the feed and metering sections. This ratio normally lies in the range of from 2 to 4, according to the type of material processed. Output rates obtainable from an extruder vary from about 10 kg/h for the smallest up to 5000 kg/h or more for the largest homogenizers. Screw-drive power requirements are usually of the order of 0.1–0.2 kW h/kg.

Many modifications to the basic form of screw design can be used, often with the aim of improving mixing. Another variant is the two-stage screw, which is effectively two screws in series. The vent of the melt at the end of the first stage, where the screw channel suddenly deepens, makes it possible to extract through a vent any air or volatiles trapped in the polymer.

Multiscrew Extrusion: In addition to single screw extruders, there are twin and multiscrew extruders performing substantially the same functions, twin-screw machines being the most common. Such extruders can have two screws intermeshing or not quite intermeshing, corotating or counterrotating. The more common intermeshing type have distinct advantages over single-screw machines in terms of an improved mixing action, and are not so much screw viscosity pumps as positive displacement pumps.

Extrusion Dies: The simplest extrusion dies are those used to make axisymmetric products such as lace and rod. The main design consideration with such dies is that changes in flow channel diameter from that of the extruder barrel bore to that of the die exit are gradual. Smooth melt flow is thus ensured, with no regions where material can be retained and degraded. In designing dies for more complicated profiles, due allowance must also be made for elastic recovery, which may cause changes in shape after the extrudates leave the dies. Other types of extrusion die are used in the production of flat film, sheet, pipe and tubular film, and in covering wire and cable.

Flat-film and Sheet Extrusion: The distinction between flat film and sheet is one of thickness, both being extruded in similar types of dies. As the widths of such flat sections are much greater than the extruder-barrel diameters, the dies must spread the melt flow laterally and produce extrudates of as uniform a thickness as possible.

Pipe, Tube and Profile Extrusion: Pipe, tube and profile extrusion process is another extrusion operation. Pipes and tubes are usually distinguished by size. Below 1.25 cm (0.5 in) diameter is called a tube; above 1.25 cm (0.5 in) diameter is called a pipe.

Wire and Cable Covering: Wire and cable covering operations are carried out over a very wide range of line speeds, from about 1 m/min for large high-voltage electrical cables to 1000 m/min or more for small-diameter wires. Nevertheless, the types of die used are similar, being of the crosshead type to accommodate the conductor entering at an angle—often a right angle—to the axis of the extruder. The success of such an arrangement depends on the design of the flow deflector, which serves to distribute the melt into a layer of uniform thickness on the conductor.

Injection Molding: The term "injection molding" as used herein denotes the process for producing substantially identical articles from a hollow mold. In the injection molding process, molten polymer is forced under high pressure into a closed mold of the required shape, where it is cooled before the mold is opened and the finished article extracted.

Blow Molding: Blow molding is used for the formation of hollow articles, such as bottles and other containers, manufactured by the blow molding process. The blow molding process involves first the formation of a molten parison, which is a preshaped sleeve, usually made by extrusion. Air is blown into the parison surrounded between two mold halves expending the parison and causing it to take the shape of the mold. The polymer solidifies and the hollow article is ejected.

Calendering: The term "calendering" as used herein denotes a process for producing continuous films or sheets by pressing molten polymer between rotating rolls.

Another process that is very important for the production of fibers and filaments is that of spinning. Melt supplied by either an extruder or gear pump is forced vertically downwards through a series of very small holes in a flat plate or spinneret, and the resulting threads are air cooled and rapidly stretched by winding at high speed on to a bobbin.

Further, the polymers and copolymer of the present invention can be worked by engineering techniques including welding, cutting and machining, although to do so to any significant extent is to lose the advantage offered by polymeric materials over metals in terms of ease of fabrication.

Having generally described this invention, a further understanding can be obtained by reference to certain specific examples which are provided herein for purposes of illustration only and are not intended to be limiting unless otherwise specified.

EXAMPLES

Example 1

Procedure for Synthesis of Poly(Succinimide-Aspartate) Copolymer in Supercritical $CO_2$ The reactor employed in this reaction was a 450 mL Parr Series 4560 Bench Top Mini Stirred Reactor, equipped with a standard impeller stirrer. A mixture of sodium aspartate and ammonium aspartate was prepared in a similar manner to that done in the thermal synthesis of poly(succinimide-aspartate) copolymer disclosed in the parent application Ser. Nos. 10/307,349 and 09/776,897 now U.S. Pat. No. 6,495,658. First, 13.3 g (0.1 mol) 1-aspartic acid was stirred with 5.1 mL 9.83 M NaOH solution (0.05 mol NaOH) and 3.25 mL of concentrated 15.43 M $NH_4OH$ (0.05 mol $NH_4OH$) in 100 mL of Nanopure $H_2O$. This mixture was stirred for 15 min and dried in a forced air oven at 80° C. for 14 hrs. After drying, the mixture was a solid with a moisture content of 3.5%. A portion of this solid (5.35 g) was ground with a mortar and pestle and added to a reactor liner. The reactor liner containing the solid was placed in the reactor and flushed with nitrogen for 1 min, then pressurized with nitrogen to 100 psi in order to test for leaks in the system. The nitrogen was vented to 10 psi. The reactor was pressurized to 787 psi from a $CO_2$ tank equipped with a syphon tube. The reactor cooling water was started, and the temperature set to 50° C. The pressure was vented to 1106 psi at 50° C., which gives a $CO_2$ density of 0.2 g/mL. The reactor temperature was set to 150° C., the stirring set to 400 RPM. The reaction was run for 4 hrs. The pressure was slowly vented to 10 psi, the reactor pressurized with nitrogen to 70 psi, and it was cooled overnight. A solid, light brown material was isolated and ground into a fine powder with a mortar and pestle (2.8 g; 68% yield after grinding). Titration by first acidifying with HCl, then titrating with NaOH showed 0.45 equivalents of carboxylate per 100 g of polymer, similar to the expected 0.43 demonstrated for poly(succinimide-aspartate) copolymer.

Example 2

Procedure for Synthesis of Polysuccinimide in Supercritical $CO_2$

Figure 2A:
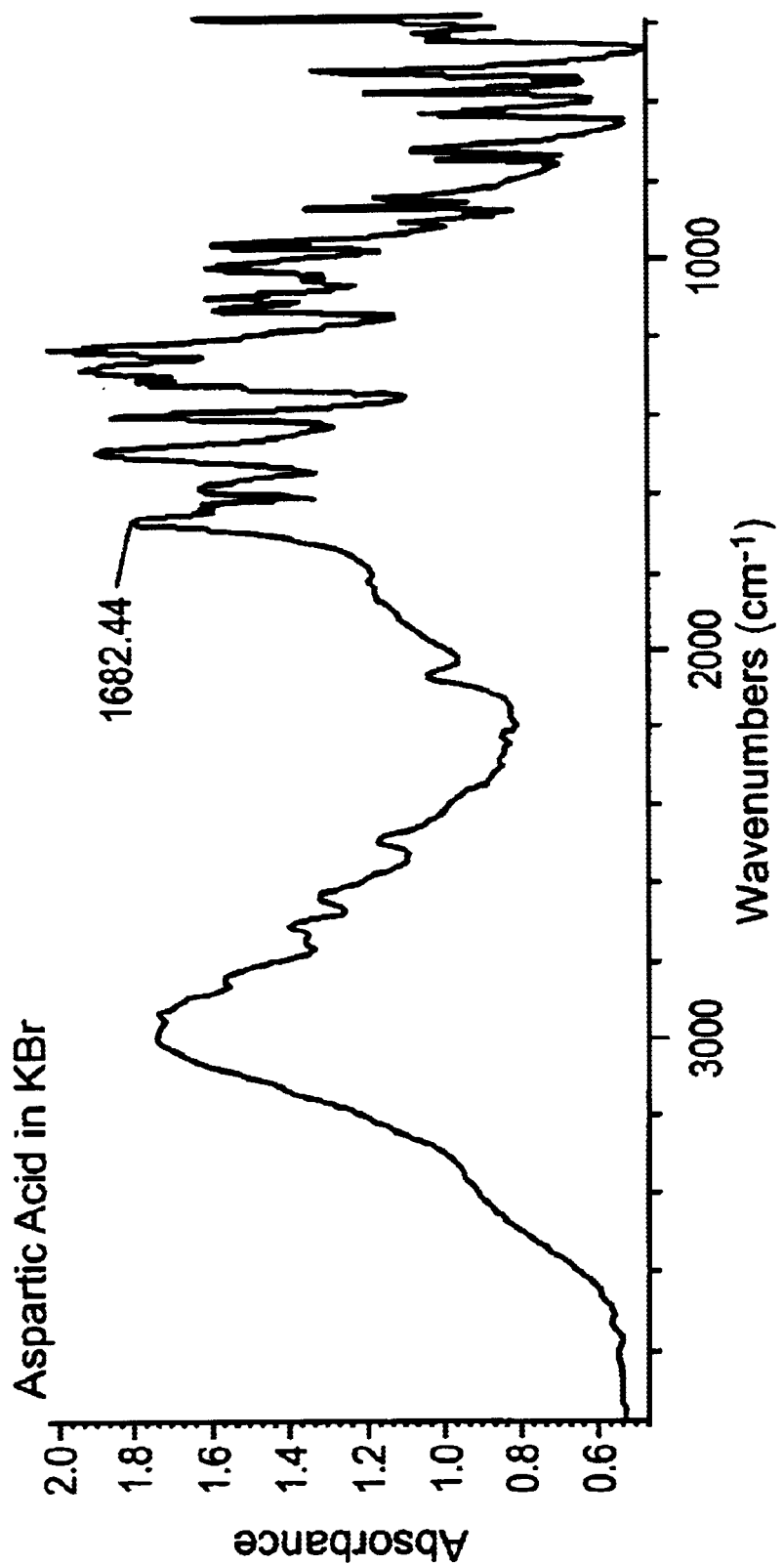
FIG. 2A depicts the IR spectra of aspartic acid.
Figure 2B:
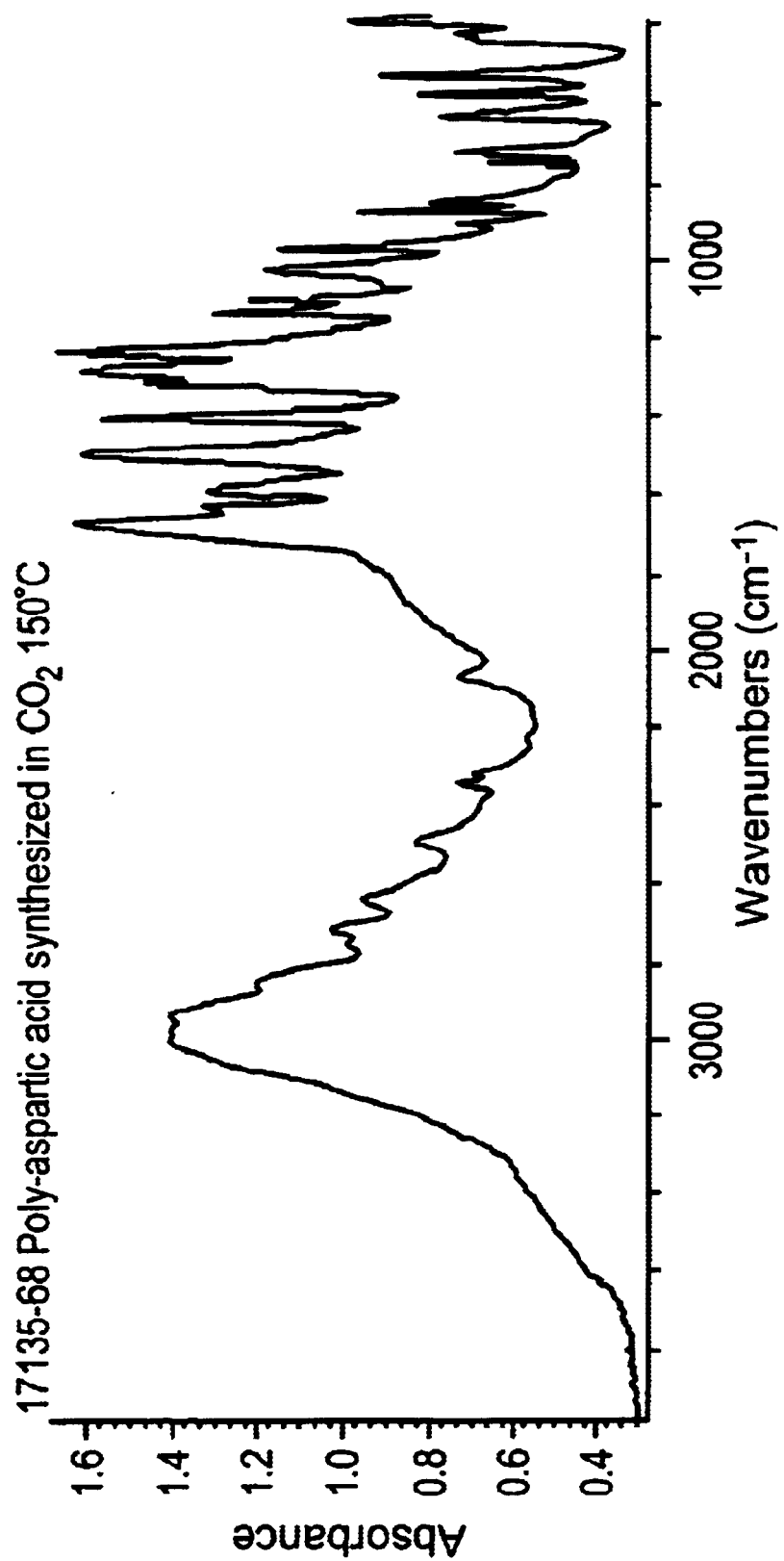
FIG. 2B depicts the IR spectra of polysuccinimide synthesized in supercritical $CO_2$ at 150° C.
Figure 3:
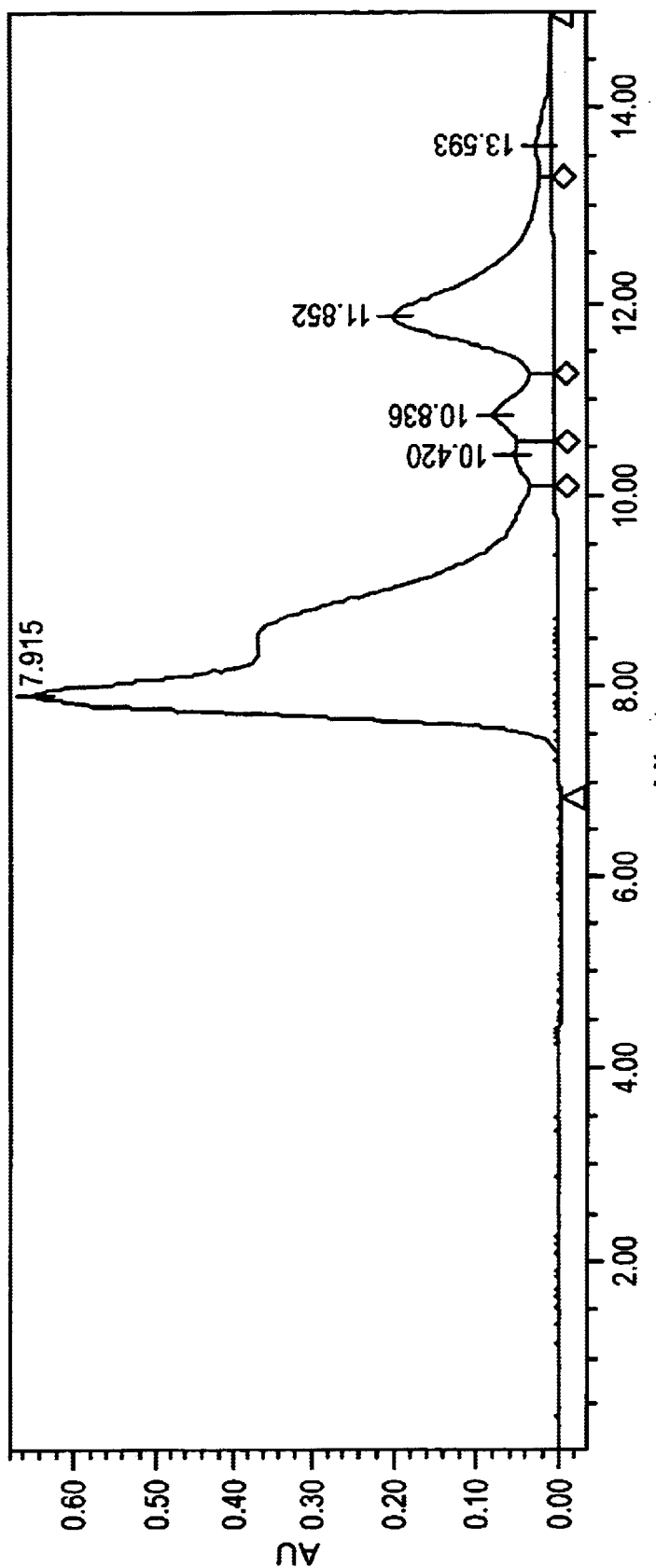
FIG. 3 is a GPC analysis of polysuccinimde synthesized in supercritical $CO_2$. The peak at 7.918 min corresponds to a MW of 4200 Daltons when compared to sodium polyacrylate standards.

The reactor employed in this reaction was a 450 mL Parr Series 4560 Bench Top Mini Stirred Reactor, equipped with a standard impeller stirrer. First, 1.58 g (0.01 mol) 1-aspartic acid was added to the reactor liner which was placed in the reactor and flushed with nitrogen for 1 min, then pressurized with nitrogen to 100 psi in order to test for leaks in the system. The nitrogen was vented to 10 psi. The reactor was pressurized to 780 psi from a $CO_2$ tank equipped with a syphon tube. The reactor cooling water was started, and the temperature set to 70° C. The pressure was vented to 1106 psi at 70° C., which gives a $CO_2$ density of 0.16 g/mL. This lower density, compared to the poly(succinimide-aspartate) copolymer synthesis, is used so the pressure limit of the reactor will not be exceeded at the higher temperatures required for this reaction. The reactor temperature was set to 205° C., the stirring set to 400 RPM. The reaction was run for 4 hrs. The pressure was slowly vented to 10 psi, the reactor pressurized with nitrogen to 116 psi, and cooled overnight. A solid, light red product was isolated and ground with a mortar and pestle (1.07 g; 78% yield after grinding). The product was characterized by IR and GPC anlaysis. The IR (FIG. 2) shows the typical expected imide peak at 1714 $cm^{-1}$. GPC analysis (FIG. 3) show that the primary product is of a MW of ~4200 Daltons.

Obviously, numerous modifications and variations of the present invention are possible in light of the above teachings. It is therefore to be understood that within the scope of the appended claims, the invention may be practiced otherwise than as specifically described herein.

What is claimed is:

1. A method for preparing a polysuccinimide, which comprises, subjecting aspartic acid to polymerization in a solvent of supercritical fluid to form a polysuccinimide; wherein said supercritical fluid is selected from the group consisting of $CO_2$, $NH_3$, $H_2O$, $N_2O$, xenon, krypton, methane, ethane, ethylene, propane, pentane, methanol, ethanol, isopropanol, isobutanol, $CClF_3$, $CFH_3$, cyclohexanol, $CS_2$, and a mixture thereof; and wherein the supercritical fluid is used in conjunction with a cosolvent; and wherein the cosolvent is selected from the group consisting of trans-2-hexenyl acetate, ethyl trans-3-hexenoate, methyl caproate, isobutyl isobutyrate, butyl acetate, butyl methacrylate, hexyl acetate, butyl butyrate, pentyl propionate, methyl ethanoate, ethyl caproate, methyl dodecanoate, 2-ethylbutyl acetate, methyl oleate, dodecyl acetate, methyl tridecanoate, soybean oil methyl esters, hexane, heptane, tetradecane, hexadecane, toluene, 1-hexadecene, 1-dodecanol, 1-nonanol and a mixture thereof.

2. The method of claim 1, wherein said supercritical fluid is maintained at a pressure of from about 500 psi to about 2500 psi.

3. The method of claim 1, wherein said supercritical fluid is maintained at a pressure of from about 700 psi to about 2000 psi.

4. The method of claim 1, wherein said supercritical fluid is maintained at a temperature of from about 50° C. to about 300° C.

5. The method of claim 1, wherein said supercritical fluid is maintained at a temperature of from about 100° C. to about 250° C.

6. The method of claim 1, wherein the weight average molecular weight of the polysuccinimide is in the order of from about 2,000 to about 10,000 Dalton.

7. The method of claim 1, wherein the weight average molecular weight of the polysuccinimide is in the order of from about 3,000 to about 5,000 Daltons.

8. The method of claim 1, wherein said polymerization is carried out in the presence of a stabilizer.

9. The method of claim 8, wherein said stabilizer is a thermal stabilizer, an antioxidant or a mixture thereof.

10. A method for preparing a polysuccinimide, which comprises, subjecting aspartic acid to polymerization in a solvent of supercritical fluid to form a polysuccinimide, wherein said polymerization is carried out in the presence of a catalyst to form the polysuccinimide.

11. The method of claim 10, wherein said catalyst is phosphoric acid.

12. The method of claim 10, wherein said polysuccinimide exhibits a weight average molecular weight of up to 300,000 Daltons.

13. A method for preparing a polysuccinimide, which comprises, subjecting aspartic acid to polymerization in a solvent of supercritical fluid to form a polysuccinimide; wherein said polysuccinimide is blended with an additive in the supercritical fluid.

14. The method of claim 13, wherein said additive is selected from the group consisting of a stabilizer, an antioxidant, a colorant, a plasticizer, a reinforcing agent, a filler, and a lubricant.

15. The method of claim 14, wherein said stabilizer is a heat stabilizer or an ultraviolet stabilizer.

16. The method of claim 14, wherein said antioxidant is selected from the group consisting of a hindered phenol, an amine, a phosphite, a thioester, a sulfite, a metal salt of a dithioacid.

17. A method for preparing a copolymer containing copolymerized aspartate units and succinimide units which comprises, subjecting a comonomer mixture of aspartic acid and a salt of aspartic acid to polymerization in a solvent of a supercritical fluid; wherein said comonomer mixture is prepared by drying a solution of a salt of aspartic acid having a cation which does not volatilize during the drying and a salt of aspartic acid having a cation which at least partially volatilizes to free aspartic acid during the drying; wherein said supercritical fluid is selected from the group consisting of $CO_2$, $NH_3$, $H_2O$, $N_2O$, xenon, krypton, methane, ethane, ethylene, propane, pentane, methanol, ethanol, isopropanol, isobutanol, $CClF_3$, $CFH_3$, cyclohexanol, $CS_2$, and a mixture thereof; and wherein the supercritical fluid solvent is used in conjunction with a cosolvent.

18. The method of claim 17, wherein the cosolvent is selected from the group consisting of trans-2-hexenyl acetate, ethyl trans-3-hexenoate, methyl caproate, isobutyl isobutyrate, butyl acetate, butyl methacrylate, and hexyl acetate, butyl butyrate, pentyl propionate, methyl ethanoate, ethyl caproate, methyl dodecanoate, 2-ethylbutyl acetate, methyl oleate, dodecyl acetate, methyl tridecanoate, soybean oil methyl esters, hexane, heptane, tetradecane, hexadecane, toluene, 1-hexadecene, 1-dodecanol, 1-nonanol and a mixture thereof.

19. The method of claim 17, wherein said supercritical fluid is maintained at a pressure of from about 500 psi to about 2500 psi.

20. The method of claim 17, wherein said supercritical fluid is maintained at a pressure of from about 700 psi to about 2000 psi.

21. The method of claim 17, wherein said supercritical fluid is maintained at a temperature of from about 50° C. to about 250° C.

22. The method of claim 17, wherein said supercritical fluid is maintained at a temperature of from about 100° C. to about 250° C.

23. The method of claim 17, wherein the weight average molecular weight of said copolymer was in the order of about 2,000 to about 10,000 Dalton.

24. The method of claim 17, wherein the weight average molecular weight of said copolymer was in the order of from about 3,000 to about 5,000 Daltons.

25. The method of claim 17, wherein said polymerization is carried out in the presence of a stabilizer.

26. The method of claim 25, wherein said stabilizer is a thermal stabilizer, an antioxidant or a mixture thereof.

27. A method for preparing a copolymer containing copolymerized aspartate units and succinimide units which comprises, subjecting a comonomer mixture of aspartic acid and a salt of aspartic acid to polymerization in a solvent of a supercritical fluid; wherein said comonomer mixture is prepared by drying a solution of a salt of aspartic acid having a cation which does not volatilize during the drying and a salt of aspartic acid having a cation which at least partially volatilizes to free aspartic acid during the drying; wherein said supercritical fluid is selected from the group consisting of $CO_2$, $NH_3$, $H_2O$, $N_2O$, xenon, krypton, methane, ethane, ethylene, propane, pentane, methanol, ethanol, isopropanol, isobutanol, $CClF_3$, $CFH_3$, cyclohexanol, $CS_2$, and a mixture thereof; wherein said polymerization is carried out in the presence of a catalyst to form the copolymer containing aspartate units and succinimide units.

28. The method of claim 27, wherein said catalyst is a Lewis acid.

29. The method of claim 27, wherein said copolymer exhibits a weight average molecular weight of up to 300,000 Daltons.

30. The method of claim 17, wherein said copolymer was blended with an additive in the supercritical fluid.

31. The method of claim 30, wherein said additive is selected from the group consisting of a stabilizer, an antioxidant, a colorant, a plasticizer, a reinforcing agent, a filler, and a lubricant.

32. The method of claim 31, wherein said stabilizer is a heat stabilizer or an ultraviolet stabilizer.

33. The method of claim 31, wherein said antioxidant is selected from the group consisting of a hindered phenol, an amine, a phosphite, a thioester, a sulfite, a metal salt of a dithioacid.

34. A method for preparing a copolymer containing succinimide moieties, which comprises, polymerizing L-aspartic acid in a supercritical fluid, in the presence of an end-capping initiator to form the copolymer.

35. The method of claim 34, wherein said end-capping initiator is selected from the group consisting of an anhydride, a carboxylic acid and an amine.

36. The method of claim 35, wherein said anhydride is selected from the group consisting of succinic anhydride, phthalic anhydride, maleic anhydride, alkenyl succinic anhydride, 1,2,4-benzenetricarboxylic anhydride; cis-1,2,3, 6-tetrahydrophthalic anhydride and 1,2-cyclohexane dicarboxylic anhydride.

37. The method of claim 35, wherein said carboxylic acid is selected from the group consisting of benzoic acid, thiolsuccinic acid and terephthalic acid.

38. The method of claim 35, wherein said amine is represented by the formula $RR_1NH$, where R, and $R_1$, are the same or different radicals selected from the group consisting of an alkyl, a substituted alkyl, an alkenyl, an aryl, aryl-alkyl, and a substitute aryl radical.

39. The method of claim 38, wherein said alkyl is selected from the group consisting of a methyl, an ethyl, a n-propyl, an isopropyl, a n-butyl, an isobutyl, a sec-butyl, a n-amyl, an isoamyl, a n-hexyl, a n-octyl, a capril, a n-decyl, a lauryl, a myristyl, a cetyl, and a stearyl.

40. The method of claim 38, wherein said substituted alkyl is hydroxyethyl.

41. The method of claim 38, wherein said alkenyl is allyl.

42. The method of claim 38, wherein said aryl is phenyl.

43. The method of claim 38, wherein said aryl-alkyl is benzyl.

44. The method of claim 38, wherein said substituted aryl is selected from the group consisting of an alkylphenyl, a chlorophenyl and a nitrophenyl.

45. The method of claim 35, wherein said amine is selected from the group consisting of an aliphatic amine, an aliphatic diamine, an aliphatic hydroxylamine, an aminoethoxylate, an aromatic amine, and an aromatic diamine.

46. The method of claim 45, wherein said aliphatic amine is selected from the group consisting of methylamine, dimethylamine, ethylamine, diethylamine, n-propylamine, di-n-propylamine, n-butylamine, n-amylamine, n-hexylamine and laurylamine.

47. The method of claim 45, wherein said aliphatic diamine is selected from the group consisting of ethylenediamine, trimethylenediamine, tetramethylenediamine, pentamethylenediamine, hexamethylenediamine.

48. The method of claim 45, wherein said aliphatic hydroxylamine is selected from the group consisting of ethanolamine, diethanolamine and triethanolamine.

49. The method of claim 45, wherein said aromatic amine is selected from the group consisting of methylaniline, dimethylaniline, diethylaniline, o-toluidine, m-toluidine and p-toluidine.

50. The method of claim 45, wherein said aromatic diamine is selected from the group consisting of o-phenylenediamine, m-phenylenediamine and p-phenylenediamine.

51. The method of claim 34, wherein said copolymer contains an anhydride end group.

52. The method of claim 51, herein said anhydride reacts with a nucleophile.

53. The method of claim 52, wherein said nucleophile is selected from the group consisting of an aminoethoxylate, a hydrophobic amine, a hydroxyl terminated materials a poly (vinyl alcohol), a polyester, a polyamide, a polysaccharide, a dextan, a cellulose, a protein, a dye and a UV absorber.

54. The method of claim 53, wherein said polysaccharide is starch.

55. The method of claim 34, wherein said copolymer is a prepolymer.

56. The method of claim 55, wherein said prepolymer exhibits a weight average molecular weight of from 100 to 1,000 Daltons.

57. The method of claim 55, wherein said prepolymer is further polymerized by a method selected from the group consisting of thermal process, a supercritical fluid process, in the molten phase and in the solid phase.

58. The method of claim 34, wherein said end-capping initiator and said L-aspartic acid are present in a ratio of from 1:1 to 1:10.

59. The method of claim 34, wherein said end-capping initiator and said L-aspartic acid are present in a ratio of from 1:1 to 1:5.

60. The method of claim 34, further comprising a monomer selected from the group consisting of an aminoacid, a hydroxy acid, a combination of a diamine with a dicarboxylate and a combination of a diol with a carboxylate.

61. The method of claim 34, wherein said copolymer is an oligomer.

62. The method of claim 34, wherein said copolymer exhibits a weight average molecular weight of from 1,000 to 150,000.

63. The method of claim 34, wherein said copolymer exhibits a weight average molecular weight of from 1,000 to 10,000.

64. The method of claim 61, wherein said oligomer undergoes chain extension in an extruder.

65. The method of claim 34, wherein a succinimide moiety of said copolymer reacts with a material selected from the group consisting of an aminoethoxylate, a hydrophobic amine and a hydroxyl terminated material to form a graft copolymer.

66. The method of claim 34, wherein an anhydride end of said copolymer further reacts with a primary or secondary amine.

67. The method of claim 34, wherein said polymerization is carried out in the presence of a stabilizer.

68. The method of claim 67, wherein said stabilizer is selected from the group consisting of a thermal stabilizer, an antioxidant and a mixture thereof.

69. A method for preparing a copolymer of L-aspartic acid, which comprises, polymerizing L-aspartic acid in a supercritical fluid, in the presence of an end-capping initiator and a catalyst to form the copolymer of L-aspartic acid.

70. The method of claim 69, wherein said catalyst is selected from the group consisting of phosphoric acid, a Lewis acid and an organometallic catalyst.

71. The method of claim 70, wherein said organometallic catalyst is tin octanoate.

72. The method of claim 34, wherein said copolymer is isolated and blended with a polymer additive.

73. The method of claim 72, wherein said polymer additive is selected from the group consisting of a stabilizer, an antioxidant, a hindered phenol, an amine, a phosphite, a thioester, a sulfite, a metal salt of a dithioacid, a colorant, a plasticizer, a reinforcing agent and a lubricant.

74. An article prepared by processing the copolymer of claim 34.

75. A method for preparing a polysuccinimide derivative, which comprises, forming said polysuccinimide in a supercritical fluid, and subjecting the polysuccinimide, in the supercritical fluid, to a ring-opening reaction.

76. The method of claim 75, wherein said ring-opening reaction is carried out in the presence of an amine.

77. The method of claim 76, further comprising water as a cosolvent.

78. The method of claim 76, wherein said amine is a combination of amines.

79. The method of claim 78, wherein said combination of amines is comprised of ammonium hydroxide and 2-aminoethanol to form a resin.

80. The method of claim 79, wherein said resin contains a free carboxylic acid salt and the amides of ammonia and aminoethanol.

81. The method of claim 76, wherein said amine has the general formula: $R_1R_2R_3N$; where $R_1$, $R_2$, and $R_3$ are the same or different radicals selected from the group consisting of hydrogen, an alkyl, a substituted alkyl, an alkenyl, an aryl, an aryl-alkyl, and a substituted aryl radical.

82. The method of claim 81, wherein said alkyl is selected from the group consisting of methyl, ethyl, n-propyl, isopropyl, n-butyl, isobutyl, sec-butyl, t-butyl, n-amyl, isoamyl, t-amyl, n-hexyl, n-octyl, capril, n-decyl, lauryl, myristyl, cetyl, and stearyl.

83. The method of claim 81, wherein said substituted alkyl is hydroxyethyl.

84. The method of claim 81, wherein said alkenyl is allyl.

85. The method of claim 81, wherein said aryl is phenyl.

86. The method of claim 81, wherein said aryl-alkyl is benzyl.

87. The method of claim 81, wherein said substituted aryl radical is selected from the group consisting of alkylphenyl, chlorophenyl and nitrophenyl.

88. The method of claim 76, wherein said amine is triethanol amine.

89. The method of claim 76, wherein said amine is selected from the group consisting of aminopyrdine, imidazole and a polyamine.

90. The method of claim 89, wherein said polyamine is selected from the group consisting of a gelatin, chitin, lysine, ornithine and melamine.

91. The method of claim 76, wherein said amine is aminoethoxylate.

92. The method of claim 75, wherein said polymerization is carried out in the presence of a stabilizer.

93. The method of claim 92, wherein said stabilizer is selected from the group consisting of a thermal stabilizer, an antioxidant and a mixture thereof.

94. The copolymer formed by the method of claim 34.

95. The derivative of the polysuccinimide formed by the method of claim 75.

96. An article prepared by processing the derivative of the copolymer of claim 34.

97. An article prepared by processing the derivative of the copolymer of claim 75.

98. The article of claim 96, wherein said processing is selected from the group consisting of extrusion, injection molding, blow molding and calendering.

99. The article of claim 97, wherein said processing is selected from the group consisting of extrusion, injection molding, blow molding and calendering.

* * * * *

UNITED STATES PATENT AND TRADEMARK OFFICE
CERTIFICATE OF CORRECTION

PATENT NO. : 6,919,421 B2
DATED : July 19, 2005
INVENTOR(S) : Graham Swift

It is certified that error appears in the above-identified patent and that said Letters Patent is hereby corrected as shown below:

Column 4,
Line 16, "a MW of 4200 Daltons" should read -- a MW of ~4200 Daltons --.

Column 12,
Lines 1-20,
"

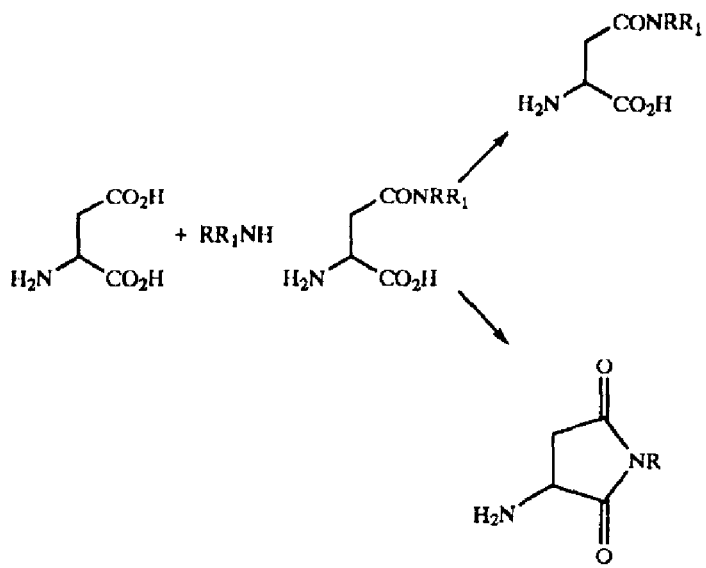

should read

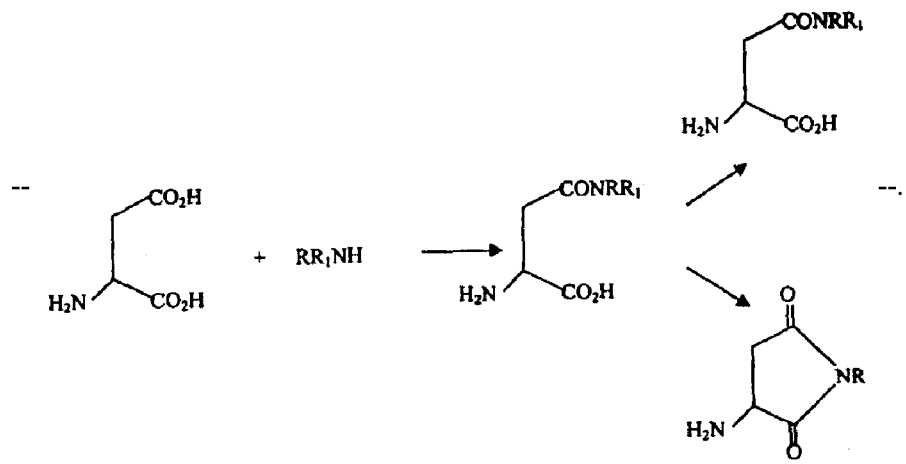

UNITED STATES PATENT AND TRADEMARK OFFICE
CERTIFICATE OF CORRECTION

PATENT NO. : 6,919,421 B2
DATED : July 19, 2005
INVENTOR(S) : Graham Swift

It is certified that error appears in the above-identified patent and that said Letters Patent is hereby corrected as shown below:

Column 15,
Line 22, "(R.)" should read -- (R•) --.
Line 30, "(RCOO.)" should read -- (RCOO•) --.

Column 21,
Line 45, "1 -nonanol" should read -- 1-nonanol --.

Signed and Sealed this

Eighteenth Day of April, 2006

JON W. DUDAS
*Director of the United States Patent and Trademark Office*